United States Patent
Gross et al.

(10) Patent No.: US 8,764,987 B2
(45) Date of Patent: Jul. 1, 2014

(54) DEVICE AND METHOD FOR DETERMINING AND CONTROLLING THE CONCENTRATION OF AT LEAST ONE SOLUTE IN A FLUID CIRCUIT

(75) Inventors: Malte Gross, Ulm (DE); Andreas Maierhofer, Schweinfurt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 286 days.

(21) Appl. No.: 13/262,407

(22) PCT Filed: Mar. 31, 2010

(86) PCT No.: PCT/EP2010/002086
§ 371 (c)(1),
(2), (4) Date: Sep. 30, 2011

(87) PCT Pub. No.: WO2010/112223
PCT Pub. Date: Oct. 7, 2010

(65) Prior Publication Data
US 2012/0018379 A1 Jan. 26, 2012

(30) Foreign Application Priority Data
Mar. 31, 2009 (DE) .......... 10 2009 015 649

(51) Int. Cl.
*B01D 61/32* (2006.01)
*B01D 61/24* (2006.01)
*B01D 61/26* (2006.01)
*B01D 61/28* (2006.01)
*A61M 1/14* (2006.01)

(52) U.S. Cl.
USPC .......... 210/746; 210/646; 210/647; 210/739; 210/103; 210/134; 210/143; 210/321.65; 604/4.01; 604/6.09

(58) Field of Classification Search
USPC .......... 210/645, 646, 647, 739, 746, 97, 103, 210/109, 134, 143, 252, 258, 321.6, 210/321.65; 604/4.01, 5.01, 6.09, 6.11, 28
See application file for complete search history.

(56) References Cited

U.S. PATENT DOCUMENTS

| | | | |
|---|---|---|---|
| 4,508,622 A | 4/1985 | Polaschegg et al. | |
| 5,024,756 A | 6/1991 | Sternby | |
| 7,563,240 B2 * | 7/2009 | Gross et al. | 604/5.01 |
| 8,211,048 B2 * | 7/2012 | Szamosfalvi et al. | 604/5.04 |
| 2001/0004523 A1 | 6/2001 | Bosetto et al. | |
| 2003/0230533 A1 * | 12/2003 | Gross et al. | 210/646 |
| 2006/0200064 A1 * | 9/2006 | Gross et al. | 604/5.01 |

FOREIGN PATENT DOCUMENTS

| | | |
|---|---|---|
| EP | 0 272 414 | 6/1988 |
| EP | 0 330 892 | 9/1989 |

* cited by examiner

*Primary Examiner* — John Kim
(74) *Attorney, Agent, or Firm* — Jacobson Holman, PLLC.

(57) ABSTRACT

An apparatus and a method for the determination and regulation of the concentration of at least one dissolved substance in a fluid circuit, in which the fluid circuit includes at least two partial circuits separated by a filter in a semi-permeable manner, includes a detection unit for determining a concentration difference of at least one first dissolved substance, a determination unit for determining the influence of at least one second dissolved substance which is not identical to the at least one first dissolved substance, and a regulation unit for regulating the concentration of the at least one dissolved substance in the fluid circuit.

18 Claims, 4 Drawing Sheets

DEVICE AND METHOD FOR DETERMINING AND CONTROLLING THE CONCENTRATION OF AT LEAST ONE SOLUTE IN A FLUID CIRCUIT

CROSS-REFERENCE TO RELATED APPLICATIONS

This is a national stage of PCT/EP10/002086 filed Mar. 31, 2010 and published in German, which claims the priority of German number 10 2009 015 649.6 filed Mar. 31, 2009, hereby incorporated by reference.

BACKGROUND OF THE INVENTION

1. Field of Invention

The present invention relates to an apparatus and to a method for the determination and regulation of the concentration of at least one dissolved substance in a fluid circuit, wherein the fluid circuit comprises at least two partial circuits, and wherein the partial circuits are separated by a filter in a semi-permeable manner.

2. Description of the Prior Art

Fluid circuit systems comprising two partial circuits, wherein one partial circuit is e.g. difficult to access, wherein an accessibility of the partial circuit is unwanted, or wherein the partial circuit is even inaccessible, and/or wherein sensors and actuators for the determination of dissolved substances and for the influencing thereof can only be attached to the accessible partial circuit usually confront the user with a problem when the concentration of a dissolved substance in the accessible partial circuit should be kept constant and/or regulated to a desired value in dependence on the actual value or desired value of the dissolved substance in the inaccessible partial circuit, but the actual value of the dissolved substance in the inaccessible partial circuit can, for example, not be determined or can only be determined with an unwarranted effort and/or is unknown.

This problem occurs in many technical areas, in particular in filtration engineering, wherein an exchange of dissolved substances from one partial circuit to another partial circuit should take place via a semi-permeable membrane.

This problem in particular arises in dialysis technology since there a monitoring and influencing of the concentration of dissolved substances such as calcium ions, sodium ions, chloride ions, etc. can admittedly take place in the dialysis circuit. It is, however, only possible with a large effort, if at all, in the blood circuit and is to a large extent even unwanted for hygienic reasons.

The problem outlined above can be illustrated easily in the case of isonatremic dialysis.

In a healthy person, the sodium concentration in the body is substantially kept constant within tight limits at a value specific to the individual by the kidney by the regulation of the electrolyte and water excretions. According to the set-point hypothesis, dialysis patients with terminal renal failure also keep their sodium concentration largely constant. Since, however, no water or sodium excretion is possible in them between the dialysis treatments, this means that every quantity of sodium ingested has the consequence of an ingestion of water due to the feeling of thirst which occurs.

In a typical hemodialysis treatment, the large part of the sodium transfer takes place convectively by the ultrafiltration since liquid whose electrolyte content corresponds to the plasma water of the patient is hereby removed from the patient. In the ideal case, this quantity corresponds to the quantity of sodium which the patient has ingested between two dialysis treatments. As a rule, the quantity of liquid the patient has ingested between the dialysis treatments is removed from him by means of ultrafiltration. The sodium concentration in the patient does not change due to the ultrafiltration. In contrast, an electrolyte transfer which can have the consequence of a change in the sodium concentration in the patient occurs due to diffusion in the dialyzer.

If the sodium concentration in the dialysate is considerably above that in the patient, sodium is supplied to the patient by diffusion during the dialysis treatment. This frequently takes place in practice either unwittingly since the sodium concentration is usually not individually adapted or intentionally to improve hemodynamic stability during the dialysis treatment.

However, the patient will again compensate the concentration disposed above his set-point after the dialysis treatment by drinking so that too high a sodium concentration during the dialysis treatment results in an increased interdialytic liquid ingestion and so to increased hyperhydration and, in some cases, to chronic high blood pressure.

To avoid the above problems, it is medically sensible to carry out an isonatremic dialysis. An isonatremic dialysis is a dialysis in which no sodium is supplied to or removed from the patient diffusely via the membrane of the dialyzer. One method for this purpose could be to determine the plasma sodium at the start of the treatment in the clinic laboratory or by means of a blood gas analyzer and to set the sodium concentration of the dialysate to a value which does not change the sodium concentration in the blood by diffusion via the filter membrane. In this respect, the Donnan effect must be taken into account which has the result that the sodium concentrations in the blood and in the dialysate differ in isonatremic dialysis.

Further basic problems occur here in addition to the problems of taking a blood sample such as labor and the laboratory costs. The measured value can differ easily by up to 3 mmol/l from the actual value due to the limited measuring accuracy of the lab methods. Furthermore, the blood gas analyzer and the clinic laboratory systematically show different values since the one process has direct potentiometry as its basis and the other process has indirect potentiometry as its basis. Furthermore, the dialysate concentrates have production tolerances which could result in lack of accuracy in the sodium concentration in the dialysate. In addition, a compensation of the tolerances in the sodium concentration in the dialysate concentrate is only possible with difficulty by measurement thereof since an exact measurement of the sodium concentration in the dialysate is practically not possible with the analyzers calibrated to blood.

The only remaining possibility for the achievement of an isonatremic dialysis would therefore be to determine the plasma sodium concentration in blood samples before and after the dialysis and to vary the sodium setting of the dialysate in a batch for so long until isonatremia has been achieved. This process is, however, not realizable for practice so that as a consequence all patients of a dialysis center are substantially treated with the same dialysate sodium.

The so-called sodium balance-neutral profiles of the dialyzer are also of no help here since the balance-neutrality only relates to the fact that the sodium transfer via the dialyzer using the profile while using the basis of a model corresponds to that of a specific fixed dialysate sodium.

Furthermore, medical considerations can require a controlled deviation from an isonatremic dialysis. This can e.g. be the case when electrolyte imbalance is present so that the set-point hypothesis of the patient is not satisfied at the then current treatment day. An increase in the plasma concentration is equally sensible in the treatment of a hyponatremic condition. Conversely, in patients who tend to excessive liquid ingestion between the dialysis treatments, a lowering of the plasma sodium below the set-point may be sensible in order thereby to reduce the feeling of thirst and so to reduce the liquid ingestion of the patient.

Solution approaches for the problems shown above are already known from the prior art, but are not yet satisfactory.

A method for the determination of the sodium content in the blood on the basis of a conductivity measurement of the dialysate is thus known from the document Petitclerc et al., "Sodium management in dialysis by conductivity", Advances in renal replacement therapy, Vol 6, No. 3 (July), 1999: pp 243-254. The fact is utilized in this respect that electrolyte balance takes place via the filter via the electrolyte exchange between blood and dialysate when there is a concentration difference of electrolytes. It is possible to detect whether an electrolyte transfer has taken place between the dialysate and the blood via the conductivity difference of the dialysate upstream and downstream of the filter. Since not only sodium exchange via the filter membranes occurs during the dialysis, but also e.g. potassium can be removed and bicarbonate added to correct the acidosis, in addition to the exchange of other electrolytes such as calcium, chlorine, etc. and non-electrolytes such as glucose and urea, the sodium content of the blood can, however, not be determined directly from the conductivity of the dialysate.

U.S. Pat. No. 4,923,613 describes a method and a machine for the determination of the sodium content of the blood of a dialysis patient by changing the dialysate composition from a time t onward such that, after a dialysate time $t+t_1$, the same conductivity is adapted downstream of the dialysate side of the dialysate filter as at the time t upstream of the dialysate side of the dialysate filter and such that the sodium content of the blood can be determined from this conductivity.

SUMMARY OF THE INVENTION

It is therefore the object of the present invention to further develop an apparatus for the regulation of the concentration of at least one dissolved substance in a fluid circuit of the initially named kind in an advantageous manner, in particular in that it allows an improved and more secure determination of the concentration change of a dissolved substance in a partial circuit which is difficult to access or is inaccessible and the regulation of a dissolved substance, preferably to an initially unknown actual value and/or desired value of the dissolved substance in the inaccessible partial circuit. In addition, the invention permits an improved and more secure determination of the concentration of the dissolved substance in the inaccessible partial circuit.

This object is achieved in accordance with the invention by an apparatus for the determination and regulation of the concentration of at least one dissolved substance in a fluid circuit that includes an extracorporeal blood circuit and a dialysate circuit having at least one filter which separates the extracorporeal blood circuit and the dialysate circuit in a semipermeable manner. Advantageous embodiments of the invention are as described herein.

Accordingly, a preferred embodiment is an apparatus which is provided for a fluid circuit of a dialysis machine. This fluid circuit comprises a dialysate circuit, in the following also called an accessible first partial circuit, and a blood circuit, in the following also called an inaccessible second partial circuit, which are separated from one another by at least one filter in a semi-permeable manner. The apparatus includes first and second means for the indirect or direct detection of the concentration of at least one dissolved substance in the dialysate circuit before and after the filter. The apparatus furthermore includes a determination unit which determines the concentration of a dissolved substance to be regulated in the blood circuit and the dialysate circuit while using previously input data specific to the patient and the determined or known concentrations of at least one dissolved substance in the dialysate circuit before and after the filter. The apparatus furthermore includes means for the regulation of the change of the concentration of the dissolved substance to be regulated in the blood circuit to a previously input desired value or dynamically to a development of specific values. The apparatus furthermore includes means for the reading in of previously stored data from a storage medium, preferably a storage card individual to the patient and means for the storage of data on this storage medium.

The desired value is preferably the desired value of the concentration change of the dissolved substance in the blood circuit which is usually difficult to access or which should not be provided with sensors for hygienic reasons.

The determination unit can advantageously have a regulation model which maps or includes the behavior of the dissolved substances in the dialysate circuit and in the vascular blood circuit of the patient, the transfer behavior of the dissolved substances via the semipermeable membrane, the time change and/or initial starting values for the iterative desired value determination while taking account of data individual to the patient as well as of the treatment parameters.

For example, the difference of the concentration of the substance to be regulated upstream and downstream of the filter can thus be determined via the indirectly or directly determined concentration differences of the same substance and/or of one and/or of more other substances in the dialysate circuit and can be regulated by means for the change of the concentration of one or more substances in the dialysate upstream of the filter. In this respect, a particularly preferred goal of the regulation is that the concentration of the substance to be regulated in the vascular blood circuit of the patient does not change during the treatment. A further preferred goal of the regulation is the constant change of the concentration of the substance to be regulated in the vascular blood circuit of the patient over the duration of the treatment around a value input by the physician which can be a concentration increase or a concentration reduction.

Provision can be made in this respect that the determination unit can be adapted dynamically and can e.g. take up changes in the supplementary conditions such as shifts in concentration. The dynamic adjustability of the determination unit preferably goes so far that the determination unit is made as a learning and/or self-adapting system. It is particularly advantageous that a regulation of the dissolved substance in the vascular blood circuit also takes place without any input of a desired value for the concentration of a dissolved substance in the vascular blood circuit, and indeed with the determined concentration change of a dissolved substance in the dialysate circuit before and after the filter and while using the available regulation model which regulates to the change of the concentration of the substance to be regulated in the blood, which is preferably zero, without a known absolute concentration of the substance to be regulated in the vascular blood circuit of the patient.

The available regulation model is in this respect advantageously designed such that it maps the regularities of the concentration distribution of dissolved substances in the blood circuit. It is in particular possible that the regularities of the substance transfer from one partial circuit to the other partial circuit via a semipermeable membrane are moreover also mapped in the regulation model.

It is furthermore possible that the detection unit does not have any further means with which the concentration of the dissolved substance can be determined in the second partial circuit.

It is furthermore conceivable that the first and second means include conductivity sensors or are made as such. Conductivity sensors have the advantage that the conductivity resulting from the sum of the dissolved substances can be determined securely and reliably.

Provision can be made that the concentration of a dissolved substance can be calculated by means of the regulation unit indirectly by the conductivity determined by means of the first and second means. It must in particular be remembered in this connection that in cases in which a single dissolved substance is present in high concentration and the remaining substances are present in a negligible or constant concentration, the substance of interest can also easily be determined from a sum value such as of the conductivity.

It is of advantage if the regulation to only a predefined fluctuation margin of the desired value in the first or second partial circuits can be limited. The setting of a predetermined fluctuation margin makes it possible to prevent concentration imbalances on at least one side of the fluid circuit during operation. It has been found in this connection that a fluctuation margin preferably within ±5%, partially up to ±10%, of the desired value is of advantage.

Provision can furthermore be made that a storage apparatus is provided upstream of the filter for the storage of an initial desired value for the dissolved substance in the vascular blood circuit of the patient and/or in the dialysate circuit, with the storage apparatus preferably including a removable storage medium. Such a removable storage medium can be a chip card in which, for example, the initial desired value for e.g. sodium in the dialysate partial circuit is stored. It is generally possible also to store further values such as all concentrations of dissolved substances as well as the conductivity resulting therefrom. Furthermore, supplementary conditions for the regulation model can be stored to enable a higher accuracy of the regulation or a faster regulation.

It is conceivable that the memory apparatus is connected to the regulation unit.

It is furthermore conceivable that the dissolved substance is represented by sodium ions.

The invention furthermore relates to a method for the determination and regulation of the concentration of at least one dissolved substance in a fluid circuit that includes an extracorporeal blood circuit and a dialysate circuit having at least one filter which separates the extracorporeal blood circuit and the dialysate circuit in a semipermeable manner. Advantageous embodiments of the method are as described herein.

This fluid circuit comprises a blood circuit and a dialysate circuit of a dialysis machine which are separated from one another by at least one filter in a semipermeable manner. Provision is accordingly made that the concentration change of a dissolved substance in the vascular blood circuit is determined indirectly or directly during a hemodialysis treatment and is regulated by suitable measures. For this purpose, the concentration difference of the substance to be regulated in the dialysate is determined indirectly or directly upstream and downstream of the filter, with a model being stored for the mapping of the contributions of other substances than that to be regulated to the indirect or direct determination of the concentration difference of the substance to be regulated. The concentration change of the substance to be regulated in the vascular blood circuit of the patient is determined by means of a model for the mapping of the substance transfer properties via the semipermeable filter. The method furthermore includes the possibility of changing the concentration of the substance to be regulated in the dialysate circuit upstream of the filter with suitable means and of adapting it such that the concentration change of this substance in the vascular blood circuit of the patient corresponds to previously input values, preferably to a zero value.

Provision can be made that the concentration of the dissolved substance in the second partial circuit is determined indirectly by determination of the conductivity in the first partial circuit.

It is particularly advantageous if the method is carried out using an apparatus in accordance with one of the embodiments thereof as described herein.

The invention additionally relates to a blood treatment apparatus having the features described herein. Provision is accordingly made that a blood treatment apparatus comprises an extracorporeal blood circuit and a dialysate circuit, with the blood circuit and the dialysate circuit being separated from one another by at least one filter in a semipermeable manner, and an apparatus in accordance with one of the embodiments thereof as described herein.

BRIEF DESCRIPTION OF THE DRAWINGS

Further details and advantages will now be explained with reference to an embodiment shown in more detail in the drawing.

There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
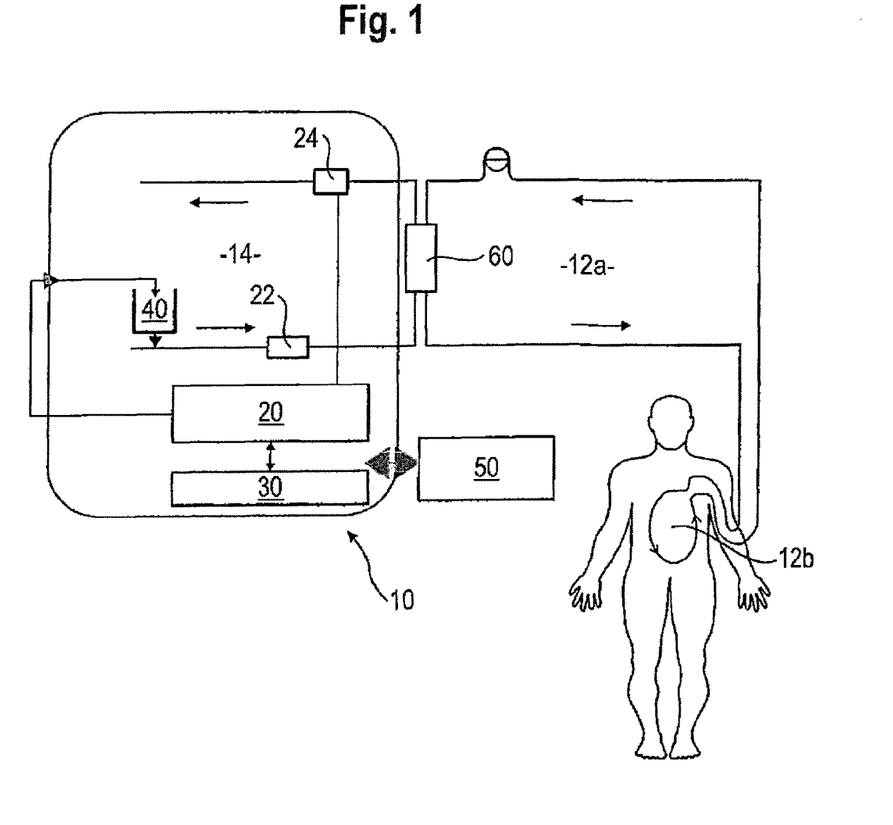
FIG. 1: a schematic representation of an apparatus for sodium balancing and regulation.

FIG. 1 shows an apparatus 10 for the determination and regulation of the concentration of at least one dissolved substance in a fluid circuit, in detail for the sodium regulation, sodium balancing and sodium display, which comprises, in addition to the components required for a dialysate circuit 14 which corresponds to a first partial circuit 14, a detection unit 20 having first and second means 22, 24 made as measurement apparatus 22, 24 for the determination of the temperature-compensated conductivity upstream and downstream of the dialyzer 60 as well as an apparatus, not shown in more detail, for the precise determination of the dialysate flow (balance chamber, flowmeter, etc.). The detection unit 20 furthermore includes a regulation unit and regulation and storage means of the regulation unit, which are not shown in any more detail, which enable a determination unit for the dynamic determination of sodium in the second partial circuit, comprising the extracorporeal blood circuit 12a and the vascular blood circuit 12b. Provision can generally also be made that the detection unit 20 and the regulation unit are made constructionally separate.

The data of the conductivity sensors 22, 24 are registered and processed by the detection unit 20 and the values for the plasma sodium concentration as well as the sodium balance are calculated. The input of user data and parameters of the regulation as well as the output of the calculated data take place via the user interface 30. The detection unit 20 furthermore contains further regulation means which continuously transfer desired values to the metering unit 40 for the dialysis concentrate on the basis of the measurement data and of the user data.

A storage apparatus 50 is furthermore provided for the storage of an initial desired value for the plasma sodium, with a chip card being able to be inserted into the storage apparatus 50. This chip card can be a patient card and can provide e.g. the stored standard values of the patient.

The determination unit of the detection unit 20 has a regulation model which includes the behavior of the dissolved substances in the second partial circuit 12a and 12b, the transfer behavior of dissolved substances via the semipermeable membrane of the dialyzer 60 as well as its time change and/or initial starting values for the iterative desired value averaging. Provision is made in this respect that the determination unit can be adapted dynamically and e.g. takes up changes in the supplementary conditions such as shifts in concentration.

It generally applies to the regulation model that the following regularities are stored or that the regulation model is based on the following regularities and is equipped with corresponding calculation means:

The mass balance relative to the flow of an electrolyte (=mass flow per time unit) $J_b$ from the patient is or can be written for the electrolyte flow on the patient side:

$$\Delta J_b = (Q_b - Q_f)c_{bo} - Q_b c_{bi} = Q_b(c_{bo} - c_{bi}) - Q_f c_{bo} \quad \text{(Equation 1)}$$

The electrolyte flow $J_d$ on the dialysate side is:

$$\Delta J_d = (Q_d + Q_f)c_{do} - Q_d c_{di} = -Q_d(c_{di} - c_{do}) + Q_f c_{do} \quad \text{(Equation 2)}$$

Where $c_{bi}$ and $c_{bo}$ are the blood side concentrations of an electrolyte before or after the dialyzer 60, $c_{di}$ and $c_{do}$ are the corresponding concentrations on the dialysate side, $Q_b$ and $Q_f$ are the blood flow or UF rate and $Q_d$ is the dialysate flow including the substitute flow.

The blood and dialysate are connected via the dialyzer membranes so that the following must apply due to the mass maintenance in the stationary state:

$$\Delta J_b + \Delta J_d = 0.$$

It thus results for the mass balance or instant electrolyte balance at the patient side in the dialysis, expressed by values at the dialysate side:

$$\Delta J_b = Q_d c_{di} - (Q_d + Q_f)c_{do} = Q_d(c_{di} - c_{do}) - Q_f c_{do} \quad \text{(Equation 3)}$$

$\Delta J > 0$ means that an electrolyte is transferred into the patient; $\Delta J < 0$ that it is removed from him.

It is assumed in simplified terms for the splitting off of the diffuse portion that the convective transport through the ultrafiltration does not influence the output concentration at the dialyzer 60. This assumption is satisfied very well for small molecules and ions in general.

It then applies to the instant diffuse electrolyte balance:

$$\Delta J_{\text{diff}} = Q_d(c_{di} - c_{do}) \quad \text{(Equation 4)}$$

It must be taken into account in the calculation of the electrolyte balance that a delay time $t_f$ passes between the inlet of fresh dialysate with the concentration $c_{do}$. This depends on the machine hydraulics, the dialyzer volume and the dialysate flow.

The electrolyte quantity transferred between the dialysate and the patient is obtained by integration while taking account of the delay time (accumulative balance while taking account of the delay time):

$$M_{\text{diff}}(t) = \int_{t=0}^{t} \Delta J_{\text{diff}}(\tau) d\tau = \quad \text{(Equation 5)}$$

$$\int_{t=0}^{t} c_{di}(\tau - t_f) Q_d(\tau - t_f) d\tau - \int_{t=0}^{t} c_{do}(\tau) Q_{do}(\tau) d\tau$$

$$M_{\text{ges}}(t) = M_{\text{diff}}(t) - \int_{t=0}^{t} c_{do}(\tau) Q_f(\tau) d\tau$$

If the distribution volume V of the patient is known, it can be estimated at any time in the 1-pool model by which amount $dc_{Pat}$ the mean electrolyte concentration in the patient has changed. This change would then also to be observed in the patient plasma after a sufficient equilibration time (concentration change in the patient).

$$dc_{Pat}(t) = \frac{M_{Diff}(t)}{V} \quad \text{(Equation 6)}$$

The diffuse flow $\Delta J_{j,\text{diff}}$ of an ion type j between the blood and the dialysate is determined by the concentration difference between the blood and the dialysate corrected by the substance-specific Donnan factor $\alpha_j$ and the substance-specific clearance $D_j$ (diffusion flow between the blood and the dialysate).

$$\Delta J_{j,\text{diff}}(t) = Q_d(c_{j,di}(t) - c_{j,do}(t)) = D_j\left(\frac{c_{j,di}(t)}{\alpha_j} - c_{j,bi}(t)\right) \quad \text{(Equation 7)}$$

The diffusion flow leads to a concentration change in the patient which moreover depends on the substance-specific number and size of the compartments in which the substance is distributed.

Since in the following the concentration development in the patient is only used for a conductivity correction on the dialysate side, a good approximation in the 1-pool model is possible within the framework of the required accuracy.

In this model, $\Delta J_{j,\text{diff}}$ in the patient with a distribution volume V results in a differential concentration change $dc_{j,bi}$:

$$dc_{j,bi} = \frac{\Delta J_{j,\text{diff}}}{V} dt.$$

The time development of the concentration in the patient $c_{j,bi}$ can thus be calculated continuously with a known starting concentration $c_{j,o}$ (calculation of the development of the ion concentration in the patient):

$$c_{j,bi}(t_0) = c_{j,0} \quad \text{(Equation 8)}$$

$$c_{j,bi}(t_n) = c_{j,bi}(t_{n-1}) + \frac{\Delta J_{j,diff}(t)}{V}(t_n - t_{n-1}).$$

The plasma-sodium concentration can be calculated on the basis of a measurement of the conductivity of the dialysate upstream and downstream of the dialyzer 60, of the dialysance D as well as the influences of the dialysate, the substitute and the ultrafiltration. In detail, it applies to the plasma conductivity:

$$\sigma_{bi} = \sigma_{di} + \frac{Q_d + Q_f + Q_s}{D}(\sigma_{do} - \sigma_{di}) \quad \text{(Equation 9)}$$

The results of the regulation as well as the user settings before the start or during the regulation can be stored internally or externally (patient card, network with database system) individual to the patient.

The temperature-compensated conductivity σ of a solution is generally a function of the concentration of all its components. In the range of the concentration occurring in the dialysate in practice, it can be approximated as a linear combination of the concentrations of its essential components (general representation of the conductivity as a function of the substance concentrations):

$$\sigma = f(c_{Na^+}, c_{K^+}, \dots ) = \sum_j c_j \gamma_j + \sigma_{Ofs} \quad \text{(Equation 10)}$$

Here, $c_j$ represents the ion concentrations and $\gamma_j$ their known molar conductivities for typical dialysate compositions and $\sigma_{Ofs}$ the offset from the linearization. Since the charge neutrality $$\sum_j c_j z_j = 0 \quad (z_j \text{ valence of the ion } j)$$

has to be ensured, the concentration of the chloride ions with $z_{Cl^-} = -1$ can be eliminated:

$$c_{Cl^-} = \sum_{j \neq Cl^-} c_j \gamma_j \Rightarrow \sigma = \sum_{j \neq Cl^-} c_j(\gamma_j + z_j \gamma_{Cl^-}) + \sigma_{Ofs}$$

In a typical dialysate composition, it therefore applies to the conductivity (linearized conversion between substance concentration and conductivity) with $$\tilde{\gamma}_j = \gamma_j + z_j \gamma_{Cl^-}:$$

$$\sigma = c_{Na^+}\tilde{\gamma}_{Na^+} + c_{K^+}\tilde{\gamma}_{K^+} + c_{Ca^{++}}\tilde{\gamma}_{Ca^{++}} + c_{Mg^{++}}\tilde{\gamma}_{Mg^{++}} + c_{Bic^-}\tilde{\gamma}_{Bic^-} + c_{Ac^-}\tilde{\gamma}_{Ac^-} + c_{Glu}\tilde{\gamma}_{Glu} + \sigma_{Ofs} \quad \text{(Equation 11)}$$

The coefficients $\tilde{\gamma}_j$ can be determined empirically from measurement data. Coefficients $\gamma_j < 0$ are conceivable, such as for glucose and urea, which is can be attributed to the fact that non-ionogenic substances disturb the movement of ions and thus reduce conductivity.

A conductivity balance can be determined very precisely by means of the conductivity sensors 22, 24 used in the dialysis machine.

A sodium balance can then be estimated from this if the change in the sodium concentration can be calculated from the conductivity change between the dialyzer inlet and outlet. For this purpose, the contribution of the concentration change of the remaining dialysate components must be estimated for the conductivity change, for which purpose the following model is used as an approximation:

1. In addition to Na$^+$ ions as well as the implicitly considered Cl$^-$ ions, essentially concentration changes of the K$^+$ ions and Bic$^-$ ions contribute to the conductivity change since generally the concentration of these ions changes the most in the patient in the course of a dialysis.
2. The change in the concentration of the remaining dialysate components does not have any real influence on the conductivity change, either because the concentration changes are too low or because the conductivity changes effected by the concentration changes of the individual components mutually compensate one another. Their concentration can therefore be assumed to be constant (see below).

The conductivity $\sigma_{di}$ at the dialyzer inlet can thus be given on the basis of equation 11:

$$\sigma_{di} = \tilde{\sigma}_{ofs}^{(di)} + \tilde{\gamma}_{Na^+} c_{Na^+}^{(di)}$$

where $$\tilde{\sigma}_{ofs}^{(di)} = c_{K^+}^{(di)}\tilde{\gamma}_{K^+} + c_{Ca^{++}}^{(di)}\tilde{\gamma}_{Ca^{++}} + c_{Mg^{++}}^{(di)}\tilde{\gamma}_{Mg^{++}} + c_{Bic^-}^{(di)}\tilde{\gamma}_{Bic^-} + c_{Ac^-}^{(di)}\tilde{\gamma}_{Ac^-} + c_{Glu}^{(di)}\tilde{\gamma}_{Glu} + \sigma_{Ofs}$$

The constant $\tilde{\sigma}_{Ofs}$ contains the contribution of all components of the fresh dialysate except for Na$^+$. It applies analogously to the conductivity $\sigma_{do}$ at the dialyzer outlet:

$$\sigma_{do} = \tilde{\sigma}_{ofs}^{(do)} + \tilde{\gamma}_{Na^+} c_{Na^+}^{(do)}$$

In accordance with the above assumptions, $\tilde{\sigma}_{ofs}^{(do)}$ can be written as $$\tilde{\sigma}_{ofs}^{(do)} = \tilde{\sigma}_{ofs}^{(di)} + \Delta\sigma_{do}$$

The contribution of the concentration change of K$^+$ and Bic$^-$ is then contained in $\Delta\sigma_{do}$ (conductivity compensation at the dialyzer outlet):

$$\Delta\sigma_{do}(t) = -\frac{1}{Q_d}(\Delta J_{K,diff}(t)\tilde{\gamma}_K + \Delta J_{Bic^-,diff}(t)\tilde{\gamma}_{Bic^-}) \quad \text{(Equation 12)}$$

In this respect, the $\Delta J_{j,diff}$ can be determined iteratively by means of equation 8 and equation 7, with j being representative of K and Bic$^-$. Inserting the sodium concentrations from the above expressions for $\sigma_{di}$ and $\sigma_{do}$ in equation 5 then produces, under the assumption that the Bic and K concentrations do not change in the time $t_f$, for the diffuse sodium balance (conductivity-based diffuse sodium balance):

$$M_{diff}^{(Na)}(t) = \frac{1}{\tilde{\gamma}_{Na^+}}\left[\int_{\tau=0}^{t}\sigma_{dr}(\tau - t_f)Q_d(\tau - t_f)d\tau - \int_{\tau=0}^{t}(\sigma_{do}(\tau) - \Delta\sigma_{do}(\tau))Q_d(\tau)d\tau\right] = \quad \text{(Equation 13)}$$

$$M_{diff}^{(LF)}(t) + M_{diff}^{(IC)}(t)$$

$$M_{diff}^{(IC)}(t) = \frac{1}{\tilde{\gamma}_{Na^+}}\left[\int_{\tau=0}^{t}\Delta\sigma_{do}(\tau)Q_d(\tau)d\tau\right]$$

-continued $$M_{diff}^{(LF)}(t) = \frac{1}{\tilde{\gamma}_{Na^+}} \left[ \int_{\tau=0}^{t} \sigma_{di}(\tau - t_f) Q_d(\tau - t_f) d\tau - \int_{\tau=0}^{t} \sigma_{do}(\tau) Q_d(\tau) d\tau \right]$$

The diffuse sodium balance can thus be broken down into a conductivity balance $M_{diff}^{(LF)}\tilde{\gamma}_{Na^+}$ which is determined directly from the conductivity measurement before and after the dialyzer 60 and into a correction term for the ion exchange via the dialyzer membrane $M_{diff}^{(Ic)}\tilde{\gamma}_{Na^+}$, which is calculated by means of a patient and dialyzer module.

It is the job of the regulation to achieve the diffuse sodium balance in the patient preset by the user by the end of the dialysis. When the set-point hypothesis is used, the goal is an isonatremic dialysis, that is, a zero sodium balance. If the zero balance should be deviated from, the user can initially preset an additional sodium quantity $M_{diff}^{(User)}(t_{End})$ which should be transferred diffusely up to the end of the treatment, $M_{diff}^{(User)}$ is >0 if NaCl should be supplied to the patient; <0 if NaCl should be removed from him. The sodium regulation distributes this quantity linearly to the time up to 30 min before the end of the UF time ($t_{End}=t_{UF}-30$ min):

$$M_{diff}^{(User)}(t) = \begin{cases} M_{diff}^{(User)}(t_{End}) \frac{t}{t_{End}} & t \le t_{End} \\ M_{diff}^{(User)}(t_{End}) & t > t_{End} \end{cases} \quad \text{(Equation 14)}$$

It is assumed in this respect that this additional sodium transfer does not influence the exchange of the other ions, even if the regulation for the realization differs from those concentration settings which were made to achieve the zero sodium balance.

The regulation must satisfy two conditions to achieve the balancing goal:
1. The diffuse sodium flow between the patient and the dialysate (see equation 4) must disappear. When taking account of a dialysate running time $t_f$ between the two conductivity sensors and the conductivity compensation for the ion displacements, this is equivalent to the demand that applies:

$$\sigma_{do}(t) - \Delta\sigma_{do}(t) = \sigma_{di}(t - t_f)$$

2. At the same time, the user preset for the diffuse balance should be satisfied at any time, with an accumulated imbalance also having to be balanced. It must therefore additionally apply (cf. equation 13):

$$M_{diss}(t) = M_{diff}^{(User)}(t).$$

These demands are realized in the determination unit or in the regulation model by a PI controller with a time lag. This first calculates the then currently to be set desired conductivity from the measured conductivity:

$$\sigma_{Soll}(t) = \sigma_{di}(t-t_f) + F_2 \tilde{\gamma}_{Na^+}((\sigma_{do}(t) - \Delta\sigma_{do}(t)) - \sigma_{di}(t-t_f)) - F_1(M_{diff}(t) - M_{diff}^{(User)}(t)) \quad \text{(Equation 15)}$$

The delay time $t_f$ is determined so that the volume element then currently located in the conductivity cell 24 disposed downstream was located in the conductivity cell 22 disposed upstream before the time $t_f$. The control variable of the controller in equation 15 therefore depends on the measured conductivity at the dialyzer inlet and outlet as well as on correction terms of a model whose parameters are initially fixed. F1 and F2 are controller constants which can be determined empirically or analytically with methods of system theory known to the skilled person so that a best possible controller behavior results, in particular in view of the step response.

The calculation of a plasma equivalent conductivity $\sigma_{bi}$ initially takes place from the measured conductivity before and after the dialyzer 60 in accordance with equation 9.

The sodium concentration is then calculated from this as the inversion of equation 11 (calculation of the plasma sodium):

$$c_{Na^+} = \frac{1}{\tilde{\gamma}_{Na^+}} \begin{pmatrix} \sigma_{bi} - c_{K^+}\tilde{\gamma}_{K^+} - c_{Ca^{++}}\tilde{\gamma}_{Ca^{++}} - c_{Mg^{++}}\tilde{\gamma}_{Mg^{++}} - \\ c_{Bic^-}\tilde{\gamma}_{Bic^-} - c_{Ac^-}\tilde{\gamma}_{Ac^-} - c_{Glu}\tilde{\gamma}_{Glu} - \sigma_{Ofs} \end{pmatrix} \quad \text{(Equation 16)}$$

In this respect, the concentrations of potassium and bicarbonate are estimated as described in equation 8 by means of an I-pool patient model. The following concentrations are assumed as constant for the other dialysate components:

$c_{Ca^{++}}=1.2$ mmol/l, $c_{Mg^{++}}=0.5$ mmol/l, $c_{Ac^-}=2.0$ mmol/l, $c_{Glu}=1.2$ g/l To be able to start the next dialysis from the start with that dialysate sodium $c_{di}^{(ZBal)}$ which is necessary for this patient for the reaching of the zero sodium balance, this value can be determined by the regulation and can be stored on the patient card at the end of the dialysis.

If the diffuse zero sodium balance was reached, $c_{di}^{(ZBal)}$ is usually equal to the desired sodium value set at the end by the regulation. It is, however, possible, that no zero balance was reached, e.g. because a sodium displacement was selected by the user or the value required to reach the zero balance could not be set within the window limits. It can equally be possible that the zero balance was admittedly reached at the end of the dialysis treatment, but that, to compensate an imbalance, the last desired sodium value differs from that value which would correspond to a zero sodium balance.

$c_{di}^{(ZBal)}$ is therefore approximated via a model. It is assumed by way of simplification here that the patient can be described by a distribution volume V which is dialyzed with respect to an average dialysate concentration $\langle c_{di} \rangle$ with $$\langle c_{di} \rangle = \int_0^T Q_d(t) c_{di}(t) dt \bigg/ \int_0^T Q_d(t) dt. \quad \text{(Equation 17)}$$

It follows from equation 6 and equation 7, while neglecting the Donnan effect:

$$c_{bi}(t) = \langle c_{di} \rangle + (c_{bi}(0) - \langle c_{di} \rangle) \exp\left(-\frac{D}{V}t\right)$$

$$M_{Diff}(t) = V * (c_{bi}(0) - c_{bi}(t)) - V\left(1 - \exp\left(-\frac{D}{V}t\right)\right)(c_{bi}(0) - \langle c_{di} \rangle)$$

A zero sodium balance ($M_{diff}(t)=0$) is reached precisely when $c_{di}^{(ZBal)}=c_{bi}(0)$. It follows from this for $c_{di}^{(ZBal)}$ $$c_{di}^{(ZBal)} = \langle c_{di} \rangle - \frac{M_{Diff}(t)}{V\left(1 - \exp\left(-\frac{D}{V}t\right)\right)} \quad \text{(Equation 18)}$$

The desired value of the sodium content of the dialysate can thus be determined from equation 18 for isonatremic dialysis and can be stored on the patient card. The detection unit 20 and the storage apparatus 50 into which the patient card(s) can be inserted are connected to data exchange means for this purpose.

The user presets the regulation range before the start of the dialysis. This can be a value for the dialysate sodium usual for the center, an estimated value for the dialysate sodium required to achieve the isonatremic state, a lab measurement of the patient sodium or a value determined by the regulation from earlier treatments. For safety reasons, the regulation is only allowed to deviate from this value during the treatment within a fixed tolerance range, e.g. +/−5%, without querying the user. If larger deviations from the preset value are required to reach the isonatremia, the user is prompted to make changes to the preset value. In addition, the distribution volume of the patient must be input for the application of the model for the correction of the diffuse balance. It can be calculated by means of an anthropometric formula or can be determined by means of bioimpedance or kinetic modeling. Furthermore, the initial concentrations of bicarbonate and potassium in the patient are required. They can come from an analysis by means of a blood gas analyzer before the start of the dialysis treatment.

All the required parameters (distribution volume, initial dialysate sodium, initial values for bicarbonate and potassium) are frequently largely the same for a patient at the start of the dialysis treatment and can therefore be stored on a patient card and can be read in at the start of the treatment in an automated fashion.

After the start of the treatment, the dialysate flow and the conductivity are determined upstream and downstream of the dialyzer 60. Furthermore, the calculation of the then current bicarbonate and potassium concentration takes place in accordance with equation 7 and equation 8, with it being assumed that the potassium clearance corresponds to the sodium clearance and that the bicarbonate clearance corresponds to 70% of the sodium clearance. The sodium clearance from the blood flow is estimated until the presence of the first clearance measurement (after approx. 20 min).

In accordance with equation 12 and equation 13, the calculation of the conductivity balance and of the correction term for the ion exchange and thus for the sodium balance then takes place from these data.

The dialysate conductivity measured upstream and downstream, the sodium balance and the correction term for the dialysate conductivity downstream of the dialyzer 60 (see equation 12) are then the input values for the sodium regulation in accordance with equation 15. The desired conductivity thus determined is finally converted into a desired value for the dialysate sodium while taking account of the composition of the dialysis concentrate and this preset value is transmitted to the metering unit 40.

Figure 2A:
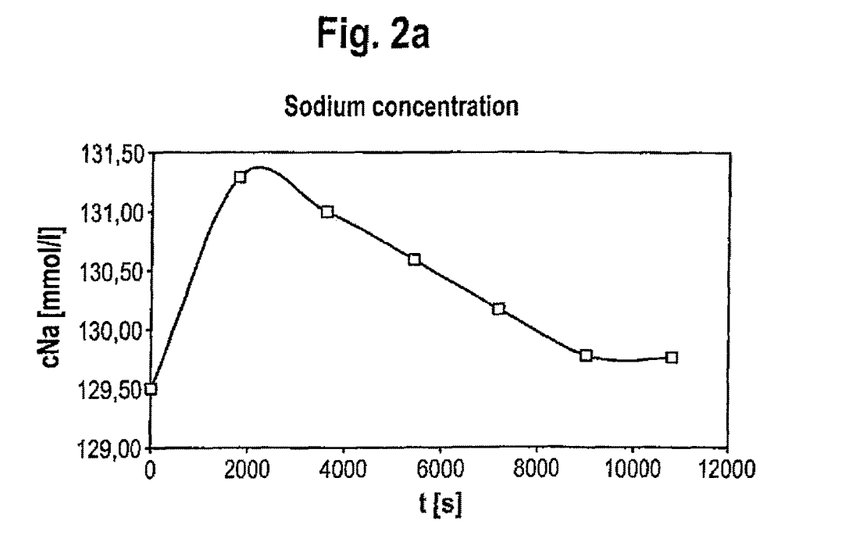
FIG. 2a: a diagram with a representation of the sodium concentration development of a simulated patient with regulation in accordance with the invention.
Figure 2B:
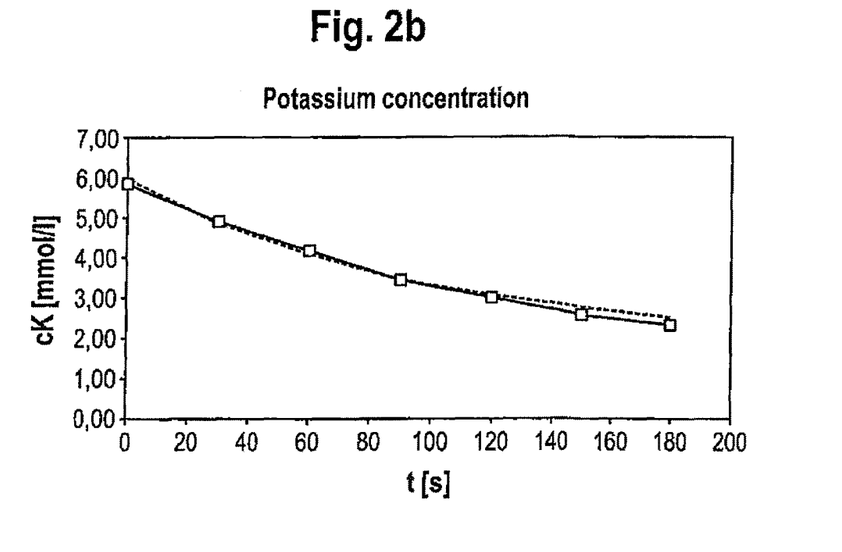
FIG. 2b: a diagram with a representation of the potassium concentration development of a simulated patient with regulation in accordance with the invention.

FIGS. 2*a* and 2*b* show the developments of the sodium and potassium concentration during a dialysis treatment for an artificial patient who was simulated by a container with 20 l saline solution while using the regulation in accordance with the invention for the sodium concentration. In this respect, the starting concentrations in the patient are 6 mmol/l potassium and 130 mmol/l sodium, for the dialysate 2 mmol/l potassium and 145 mmol/l sodium. The regulation in accordance with the invention adapts the dialysate composition such that the sodium concentration changes as little as possible over the dialysis duration, as shown in FIG. 2*a*. FIG. 2*b* shows the development of the potassium concentration in the patient, with the solid line representing measured values and the broken line representing the values calculated by the model. A regulation which only keeps the conductivity of the dialysate constant would compensate the loss of approx 3.5 mmol/l potassium by the supply of approx. 4.5 mmol/l sodium in the present example, which would result in an unwanted increase in the sodium concentration in the patient. The regulation in accordance with the invention keeps the sodium concentration in the patient approximately constant even though the concentrations of sodium and potassium in the dialysate differ greatly from that in the blood of the patient at the start of the dialysis.

Figure 3:
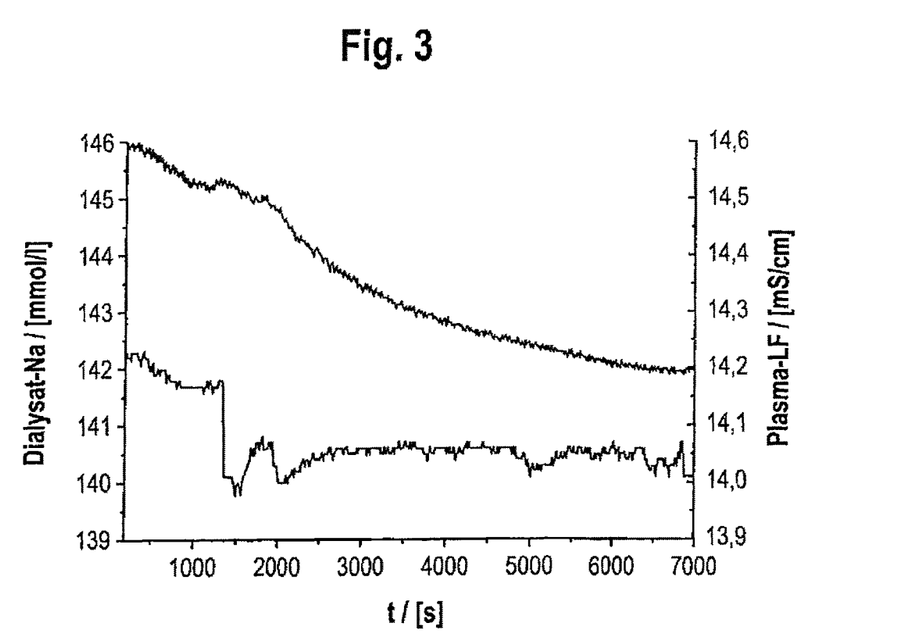
FIG. 3: a diagram with a representation of the measurement curves for the zero sodium balance regulation.

FIG. 3 shows a lab experiment in vitro for zero sodium balance regulation using the compensation for the exchange of potassium and bicarbonate. The desired value of the regulation is shown for the dialysate sodium (lower curve, left hand scale) as well as the measured development of the conductivity in the model patient (upper curve, right hand scale). The model patient (distribution volume 10 l) had 14.6 mS/cm at the start o the conductivity. Without compensation, the regulation would therefore have set a dialysate sodium of approx. 146 mmol/l and would have kept the conductivity constant with the present dialysate composition. Transferred to a patient, the conductivity drop due to potassium loss and ingestion of bicarbonate would in this connection be compensated by a supply of sodium so that the final sodium would have been much higher than the starting sodium.

By use of the compensation, the regulation already sets a much lower sodium value at the start of the treatment and keeps this largely constant. The drop in the conductivity of the patient corresponds to the situation that the value of the plasma sodium admittedly remains constant, but the plasma conductivity falls due to potassium loss and ingestion of bicarbonate.

Figure 4:
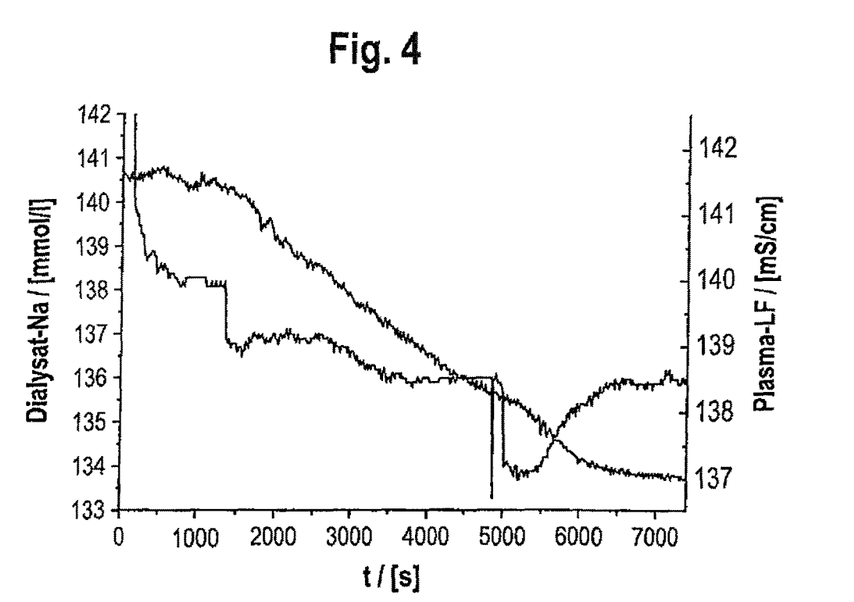
FIG. 4: a diagram with a representation of the measurement curves for the controlled sodium removal.

FIG. 4 shows an in vitro lab experiment for the user-defined removal of NaCl. In contrast to the prior art, according to which only the regulation of the plasma sodium to a preset value is possible, the user can initiate relative changes to the then current value of the plasma sodium, i.e. set the extent to which it is possible to deviate from the isonatremic state. For this purpose, the distribution volume of the patient must be input or read from a data carrier. In addition, the treatment duration typically has to be given as the duration of the ultrafiltration. The user can now give a desired value for the sodium concentration change in mmol/l. Equally, the initial values of potassium and bicarbonate are required so that the correction of the balancing described above can be carried out.

It is then distributed linearly over the planned treatment duration by the regulation as likewise described above. In this connection, changes in the clearance and changes in the conductivity caused by the ion exchange are taken into account automatically in the course of the treatment. This results in a treatment with largely constant diffusion gradients between the plasma and the dialysate. Alternatively, the user can also preset a total sodium quantity which should be removed from or supplied to the patient during the dialysis by ultrafiltration and by diffusion. This is useful for applications in which the sodium ingestion between the dialyses is known precisely due to the diet.

FIG. 4 shows an in vitro lab experiment for the user-defined removal of NaCl (user preset 4.5 mmol/l) from a model patient (NaCl solution, distribution volume 10 l). In this connection, the curve extending at the bottom in the left hand part illustrates the desired value of the regulation for the dialysate sodium and the curve extending at the top illustrates the measured extent of the conductivity in the model patient. No compensation for the ion exchange was carried out in the experiment so that the development of the dialysate sodium set by the regulation was only caused by the algorithm to achieve the concentration displacement. The constant value of the dialysate sodium at approx. 3500 s is created in that the lower end of the regulation range was reached at this point in time. Only at 5000 s was this displaced by the user toward lower sodium concentrations so that as a consequence the "making up" of the planned sodium withdrawal took place.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. An apparatus for the determination and regulation of the concentration of at least one dissolved substance in a fluid circuit, the fluid circuit including an extracorporeal blood circuit and a dialysate circuit having at least one filter which separates the extracorporeal blood circuit and the dialysate circuit in a semipermeable manner, said apparatus comprising:
   a detection unit having at least a first determining element with which a concentration difference of at least one first dissolved substance can be determined indirectly and/or directly by the detection unit before and after the filter in the dialysate circuit;
   a determination unit which determines an influence of at least one second dissolved substance, which is not identical to the at least one first dissolved substance, on the first determining element of the detection unit while using a model and calculates the concentration difference of the at least one first dissolved substance before and after the filter in the dialysate circuit; and
   a regulation unit for regulating the concentration of the at least one dissolved substance in the fluid circuit,
   the regulation unit including a regulation element and a storage element, with an actual value of the determined concentration difference of the at least one first dissolved substance in the dialysate circuit being calibrated by the regulation element with respect to a desired value for the concentration or for a concentration change of the at least one first dissolved substance in the extracorporeal blood circuit or in a vascular blood circuit, and the concentration of the at least one first dissolved substance in the dialysate circuit being regulated to a desired value via the regulation element, or with a desired value for the concentration of the at least one first dissolved substance in the dialysate circuit upstream of the filter being determined by the regulation element from the actual value of the determined concentration difference of the at least one first substance in the dialysate circuit before and after the filter, and the concentration of the at least one first dissolved substance in the dialysate circuit upstream of the filter being regulated to the desired value via the regulation unit.

2. The apparatus in accordance with claim 1, wherein the detection unit includes at least a second determining element with which the concentration difference of the at least one first dissolved substance can be determined indirectly and/or directly by the detection unit before and after the filter in the dialysate circuit, with the second determining element being arranged upstream and the first determining element being arranged downstream of the filter.

3. The apparatus in accordance with claim 1, wherein the desired value for the concentration of the at least one dissolved substance can be determined in the dialysate circuit upstream of the filter.

4. The apparatus in accordance with claim 2, wherein at least one of the first and/or and the second determining elements includes conductivity sensors, or is configured as a conductivity sensor.

5. The apparatus in accordance with claim 4, wherein the concentration of the at least one first dissolved substance can be determined indirectly by the conductivity determined via at least one of the first determining element and the second determining element via the regulation unit.

6. The apparatus in accordance with claim 1, wherein the concentration of the at least one first dissolved substance can be regulated to the desired value in the dialysate circuit upstream of the filter via the regulation element.

7. The apparatus in accordance with claim 1, wherein the concentration of the at least one first dissolved substance can be regulated to a second desired value differing from the desired value in the dialysate circuit upstream of the filter via the regulation element.

8. The apparatus in accordance with claim 1, wherein the regulation can be limited only to a predefined fluctuation margin in the extracorporeal blood circuit and the dialysate circuit.

9. The apparatus in accordance with claim 1, further comprising a storage apparatus for storing an initial desired value of the dissolved substance.

10. The apparatus in accordance with claim 9, wherein the storage apparatus is connected to the regulation unit.

11. The apparatus in accordance with claim 1, wherein the apparatus is a component of a dialysis machine.

12. A method for the determination and regulation of the concentration of at least one dissolved substance in a fluid circuit, the fluid circuit including an an extracorporeal blood circuit and a dialysate circuit having at least one filter which separates the extracorporeal blood circuit and the dialysate circuit in a semipermeable manner, said method comprising:
   determining a concentration difference of at least one first dissolved substance indirectly and/or directly via a detection unit having at least one determining element before and after the filter in the dialysate circuit;
   determining with a determination unit an influence of at least one second dissolved substance, which is not identical to the at least one first dissolved substance, on the determining element of the detection unit while using a model and calculating the concentration difference of the at least one first dissolved substance before and after the filter in the dialysate circuit; and
   regulating with a regulation unit the concentration of the at least one dissolved substance in the fluid circuit,
   the regulation unit including a regulation element and a storage element, with an actual value of the determined concentration difference of the at least one first dissolved substance in the dialysate circuit being calibrated by the regulation element with respect to a desired value for the concentration or for a concentration change of the at least one first dissolved substance in the extracorporeal blood circuit or in a vascular blood circuit, and the concentration of the at least one first dissolved substance in the dialysate circuit being regulated to a desired value via the regulation element, or with a desired value for the concentration of the at least one first dissolved substance in the dialysate circuit upstream of the filter being determined by the regulation element from the actual value of the determined concentration difference of the at least one first substance in the dialysate circuit before and after the filter, and the concentration of the at least one first dissolved substance in the dialysate circuit upstream of the filter being regulated to the desired value via the regulation unit.

13. The method in accordance with claim 12, wherein the detection unit includes at least a second determining element with which the concentration difference of the at least one first dissolved substance is determined indirectly and/or directly by the detection unit before and after the filter in the dialysate circuit, with the second determining element being arranged upstream and the first determining element being arranged downstream of the filter; and/or wherein the desired value for the concentration of the at least one dissolved substance is determined upstream of the filter in the dialysate circuit.

14. The method in accordance with claim 12, wherein the concentration of the dissolved substance in the extracorporeal blood circuit is determined indirectly by determination of the conductivity in the dialysate circuit.

15. A blood treatment apparatus comprising an extracorporeal blood circuit and a dialysate circuit, wherein the blood circuit and the dialysate circuit are separated from one another by at least one filter in a semipermeable manner, and an apparatus in accordance with claim 1.

16. The apparatus in accordance with claim 8, wherein the predefined fluctuation margin is within ±5% of the desired value.

17. The apparatus in accordance with claim 9, wherein the storage apparatus includes a removable storage medium.

18. The apparatus in accordance with claim 1, wherein the dissolved substance represents sodium ions.

* * * * *